(12) United States Patent
Ting

(10) Patent No.: US 7,505,554 B2
(45) Date of Patent: Mar. 17, 2009

(54) APPARATUS AND METHODS OF AN X-RAY AND TOMOSYNTHESIS AND DUAL SPECTRA MACHINE

(75) Inventor: Rulei Ting, Holmdel, NJ (US)

(73) Assignee: DigiMD Corporation, Holmdel, NJ (US)

( * ) Notice: Subject to any disclaimer, the term of this patent is extended or adjusted under 35 U.S.C. 154(b) by 0 days.

(21) Appl. No.: 11/255,289

(22) Filed: Oct. 20, 2005

(65) Prior Publication Data
US 2007/0019784 A1    Jan. 25, 2007

Related U.S. Application Data

(60) Provisional application No. 60/775,972, filed on Jul. 25, 2005.

(51) Int. Cl.
*A61B 6/03* (2006.01)
*H01L 27/146* (2006.01)

(52) U.S. Cl. .................. 378/19; 250/370.09

(58) Field of Classification Search ............ 378/19–23, 378/25, 26, 51, 55, 62, 145–148, 156–158, 378/4, 11–14, 98.8, 196, 197, 116; 600/425; 250/361 R, 362, 363.01, 363.04, 370.08, 250/370.09
See application file for complete search history.

(56) References Cited

U.S. PATENT DOCUMENTS

| | | | | |
|---|---|---|---|---|
| 4,037,585 A * | 7/1977 | Gildenberg | .................... | 378/8 |
| 4,138,721 A * | 2/1979 | Boyd | .......................... | 378/14 |
| 4,845,731 A * | 7/1989 | Vidmar et al. | ................ | 378/98 |
| 5,054,048 A | 10/1991 | Wang | .......................... | 378/146 |
| 5,132,995 A * | 7/1992 | Stein | ............................ | 378/56 |
| 5,365,562 A | 11/1994 | Toker | ......................... | 378/37 |
| 5,430,784 A | 7/1995 | Ribner et al. | ............... | 378/19 |
| 5,493,593 A * | 2/1996 | Muller et al. | ................. | 378/19 |
| 5,526,394 A | 6/1996 | Siczek et al. | ................. | 378/37 |
| 5,583,904 A * | 12/1996 | Adams | ........................ | 378/22 |
| 5,651,047 A * | 7/1997 | Moorman et al. | .......... | 378/98.8 |
| 5,838,758 A * | 11/1998 | Krug et al. | .................... | 378/53 |
| 5,864,146 A * | 1/1999 | Karellas | ..................... | 250/581 |
| 5,872,828 A | 2/1999 | Niklason et al. | .............. | 378/23 |
| 5,917,881 A | 6/1999 | Jeffery | ...................... | 378/98.8 |
| 6,028,910 A * | 2/2000 | Kirchner et al. | ............... | 378/22 |
| 6,173,003 B1 | 1/2001 | Whikehart et al. | .......... | 375/130 |
| 6,175,611 B1 * | 1/2001 | Melen et al. | .................. | 378/19 |
| 6,178,223 B1 * | 1/2001 | Solomon et al. | ............. | 378/62 |
| 6,233,305 B1 | 5/2001 | Muller | ........................ | 378/21 |
| 6,256,370 B1 | 7/2001 | Yavuz | ........................ | 378/22 |
| 6,289,235 B1 | 9/2001 | Webber et al. | ............. | 600/426 |
| 6,292,531 B1 * | 9/2001 | Hsieh | .......................... | 378/37 |
| 6,292,534 B1 | 9/2001 | Linders et al. | ............. | 378/98.2 |
| 6,324,249 B1 | 11/2001 | Fazzio | .......................... | 378/22 |
| 6,332,015 B1 * | 12/2001 | Honda | ..................... | 378/98.11 |
| 6,341,156 B1 * | 1/2002 | Baetz et al. | ................ | 378/98.8 |

(Continued)

*Primary Examiner*—Edward J Glick
*Assistant Examiner*—Anastasia Midkiff
(74) *Attorney, Agent, or Firm*—Woodcock Washburn LLP

(57) ABSTRACT

An X-ray device, array and method for performing digital X-ray imaging. An X-ray device has an X-ray source that is disposed on a substantially opposite side of an object to be analyzed from a digital X-ray detector. The digital X-ray detector may be formed as an array having a plurality of detectors, and the device may have a plurality of arrays. The detector moves linearly relative to the object along an axis.

34 Claims, 16 Drawing Sheets

U.S. PATENT DOCUMENTS

| | | | |
|---|---|---|---|
| 6,375,352 B1 | 4/2002 | Hewes et al. | 378/196 |
| 6,483,890 B1 | 11/2002 | Malamud | 378/22 |
| 6,496,557 B2 * | 12/2002 | Wilson et al. | 378/21 |
| 6,510,195 B1 * | 1/2003 | Chappo et al. | 378/19 |
| 6,570,954 B2 | 5/2003 | Rasche et al. | 378/21 |
| 6,628,746 B2 | 9/2003 | Eppler et al. | 378/21 |
| 6,647,092 B2 | 11/2003 | Eberhard et al. | 378/65 |
| 6,760,404 B2 * | 7/2004 | Saito et al. | 378/98.8 |
| 6,842,502 B2 | 1/2005 | Jaffray et al. | 378/65 |
| 6,862,337 B2 | 3/2005 | Claus et al. | 378/26 |
| 6,865,249 B2 | 3/2005 | Mehldau | 378/8 |
| 6,868,138 B2 | 3/2005 | Clinthorne et al. | 378/98.8 |
| 6,956,925 B1 * | 10/2005 | Hoffman | 378/4 |
| 6,973,158 B2 * | 12/2005 | Besson | 378/16 |
| 2002/0141532 A1 | 10/2002 | Koppe et al. | 378/21 |
| 2002/0191750 A1 * | 12/2002 | Wang et al. | 378/152 |
| 2003/0058983 A1 | 3/2003 | Thayer | 378/19 |
| 2003/0164888 A1 | 9/2003 | Orava et al. | 348/308 |
| 2003/0200655 A1 | 10/2003 | Vafi et al. | 29/854 |
| 2003/0235265 A1 * | 12/2003 | Clinthorne et al. | 378/4 |
| 2004/0007671 A1 | 1/2004 | Sipila et al. | 250/370.01 |
| 2004/0008810 A1 | 1/2004 | Nelson et al. | 378/19 |
| 2004/0066882 A1 | 4/2004 | Eberhard et al. | 378/19 |
| 2004/0066884 A1 | 4/2004 | Hermann et al. | 378/27 |
| 2004/0120453 A1 * | 6/2004 | Vafi et al. | 378/19 |
| 2004/0136493 A1 * | 7/2004 | Konno et al. | 378/19 |
| 2004/0156476 A1 | 8/2004 | Halsmer et al. | 378/146 |
| 2004/0252811 A1 | 12/2004 | Morita et al. | 378/207 |
| 2004/0264626 A1 * | 12/2004 | Besson | 378/4 |
| 2004/0264628 A1 | 12/2004 | Besson | 378/5 |
| 2004/0264636 A1 * | 12/2004 | Claus et al. | 378/26 |
| 2005/0041781 A1 | 2/2005 | Jefferson | 378/210 |
| 2005/0105687 A1 | 5/2005 | Heismann et al. | 378/98.8 |
| 2005/0113681 A1 | 5/2005 | DeFreitas et al. | 600/426 |
| 2005/0135560 A1 | 6/2005 | Dafni et al. | 378/101 |
| 2005/0152491 A1 | 7/2005 | Francke et al. | 378/4 |
| 2005/0156114 A1 | 7/2005 | Yokoi et al. | 250/370.09 |
| 2005/0185755 A1 * | 8/2005 | Okamura | 378/22 |
| 2005/0226375 A1 * | 10/2005 | Eberhard et al. | 378/62 |
| 2006/0065841 A1 * | 3/2006 | Hietanen et al. | 250/370.09 |

* cited by examiner

APPARATUS AND METHODS OF AN X-RAY AND TOMOSYNTHESIS AND DUAL SPECTRA MACHINE

CROSS-REFERENCE TO RELATED APPLICATION

This application claims priority under 35 U.S.C. §119(e) to U.S. Patent Application No. 60/775,972, filed Jul. 25, 2005, titled "Apparatus And Methods Of An X-Ray And Tomosynthesis And Dual Spectra Machine," the disclosure of which is hereby incorporated by reference as if set forth fully herein.

FIELD OF THE INVENTION

The present invention relates generally to X-ray imaging. More particularly, the present invention relates to digital X-ray imaging techniques and apparatus.

BACKGROUND OF THE INVENTION

X-ray devices have been used for many years in medical, security and other applications. Conventional, analog X-ray devices employ an X-ray source and photographic film, which are placed on either side of an object to be examined. The X-rays are absorbed, scattered or unaffected as they pass through the object, depending on the density of features within the object. The film captures the X-rays, thereby creating an attenuation image of the features.

While analog X-ray devices are effective for some applications, the need to use chemical-based film causes them to be disfavored in applications where multiple images need to be produced rapidly or even continuously, as is the case with security X-ray machines. In addition, analog film images cannot be easily manipulated by a computer, thereby often requiring an additional step before digital storage, analysis and/or manipulation of the X-ray data can occur.

Thus, digital X-ray technology replaces the film that is used in analog X-ray devices with a digital detector. The digital detector detects the X-rays after they have passed through the object and generates electrical signals that can be interpreted by a computer to produce a corresponding image. Thus, the image may be generated very quickly (e.g., in real-time), can be digitally stored and can even be used to generate continuous images. In addition, digital X-ray technology provides higher detective quantum efficiency ("DQE") and larger dynamic range, as is known to those skilled in the art. Therefore, digital X-ray technology enables better quality images when compared to analog X-ray technology.

Both analog and digital X-ray technology, however, collapse 3-D features into 2-D plane images, which causes the overlap of features within the object. While 2-D images may be acceptable in some applications, this overlapping of features, commonly referred to as "structured noise," can become problematic in some medical lesion diagnosis and other applications. Lesions tend to provide a lower level of visual contrast in 2-D X-ray images because their density is similar to that of surrounding tissue. Thus, a low contrast lesion may be hidden behind dense, and therefore higher-contrast, tissue such as bone. In the case of mammography, false negative and false positive test results are quite common because of the poor contrast provided by conventional 2-D X-ray techniques, whether analog or digital.

A conventional solution to the problem of poor image contrast is to employ a technique that enables material decomposition, where an object is subjected to X-rays of varying X-ray photon energy spectra. As a result, object features of different compositions will interact with the X-rays differently, depending on the photon energy, thereby creating images with differently-emphasized features. Typically, material decomposition (or an atomic number Z and corresponding density calculation) separates an image into two images corresponding to two base materials, where the two base materials have distinct X-ray attenuation characteristics. To perform such a material separation, two distinctive incident X-ray spectra are needed to measure the same object. Conventionally, such distinctive spectra are produced with two different tube high voltage settings, or at the same tube high voltage setting but using two different beam filtration materials. A shortcoming of such material decomposition methods is that such methods mainly work on tissues that have different X-ray attenuation coefficients, such as bone and soft tissue, and are not very sensitive to slight material composition changes.

Because the image data generated by a digital detector is digital in nature, a computer may be used to manipulate the data to create additional images that may be able to isolate desired features. For example, in conventional tomosynthesis, multiple views of an object are taken at several projection angles with a large area digital detector panel. A "shift-and-add" algorithm may then be applied on the digital data to focus on a slice depth, where out-of-plane features are de-emphasized and in-plane features are enhanced. Thus, while each slice image is still 2-D, the ability to de-emphasize out-of-plane features reduces the effects of such features so as to enable images of higher quality. A typical system implementation usually has more than 10 projection angles to further enhance the focusing accuracy.

In Computerized Axial Tomography (CAT), for example, a series of radially-oriented view projection images are taken of a patient at various angles and input into a computer. The computer applies mathematical algorithms to the image data to create additional representations of the object. As a result, the digital image data may be electronically manipulated to generate the best view for the intended application (e.g., cross-sectional images generated from projection image data). Thus, visual contrast between features within an object may be increased.

Digital X-ray technology typically requires a detector area of approximately 45 cm by 45 cm for chest radiography and 25 cm by 30 cm for mammography for properly-sized images. Often, smaller detectors cannot be used because the inevitable gaps between the detectors results in lost data and therefore poor quality images. Unfortunately, fabrication of large field digital X-ray detectors is often difficult and expensive. In addition, digital detectors having the sizes discussed above (referred to as "large field" detectors) typically have a pixel size ranging from 50 μm to 200 μm. While this level of resolution may be sufficient for some applications, other applications such as mammography require even higher resolutions for effective diagnosis. Because they are easier to manufacture, small-field digital detectors can achieve smaller pixel sizes, which therefore yields greater image resolution.

An additional shortcoming of a typical tomosynthesis device is that the device's X-ray source must be rotated, which adds to the complexity, size and cost of such a device. For example, a CAT scan machine has a gantry within which an X-ray source and large digital detector are placed on opposite sides of an object to be analyzed. The gantry rotates the X-ray source and digital detector to enable numerous images of the object that is positioned within the gantry at different view angles. The rotating gantry assembly is a complex mechanism that is very expensive to construct and maintain.

Also, vibrations caused by the rotating gantry may adversely affect the alignment of the X-ray source and the digital detector, thereby necessitating a robust, vibration-reducing design that needs to be maintained very precisely. In addition, conventional CAT scan machines are very large and therefore require a specialized and substantially permanent site, as well as a high-voltage power supply. The large size of a CAT scan machine further renders it unwieldy or unusable when attempting to obtain images of smaller body parts, as is the case in mammography.

SUMMARY OF THE INVENTION

According to one embodiment of the present invention, a digital X-ray device has an X-ray source mounted opposite an array of digital X-ray detectors. The detectors are oriented longitudinally to form the array and are configured to provide overlapping coverage between adjoining detectors when the array is moved relative to an object to be analyzed. The detector region of the device may have any number of arrays arranged in parallel to each other.

According to another embodiment, an object to be analyzed may be placed between the X-ray source and a digital X-ray detector, or one or more digital X-ray detectors. To capture a 2-D X-ray image, the X-ray source may remain stationary while emitting X-rays, and the detector may move linearly relative to the object being analyzed while capturing data. Alternatively, the detector may remain stationary while the X-ray source moves linearly. To capture data for producing images by way of tomosynthesis, the X-ray source and detector move linearly in unison, relative to the object. In the context of either 2-D X-ray imaging or tomosynthesis, material decomposition may be enabled by placing a set of filter materials proximate the X-ray source or the detector. In an embodiment, more than one set of filter materials may be so designed to enable optimized material decomposition images to be taken during a single pass of the X-ray source and/or detector.

DETAILED DESCRIPTION OF ILLUSTRATIVE EMBODIMENTS

It will be appreciated that a person familiar with digital X-ray imaging should be familiar with image processing algorithms and methods, as well as their use in connection with the generation of images from digital X-ray data. In addition, such a person should be familiar with tomosynthesis image processing. Accordingly, details relating to such topics are omitted herein for clarity.

Figure 1A:
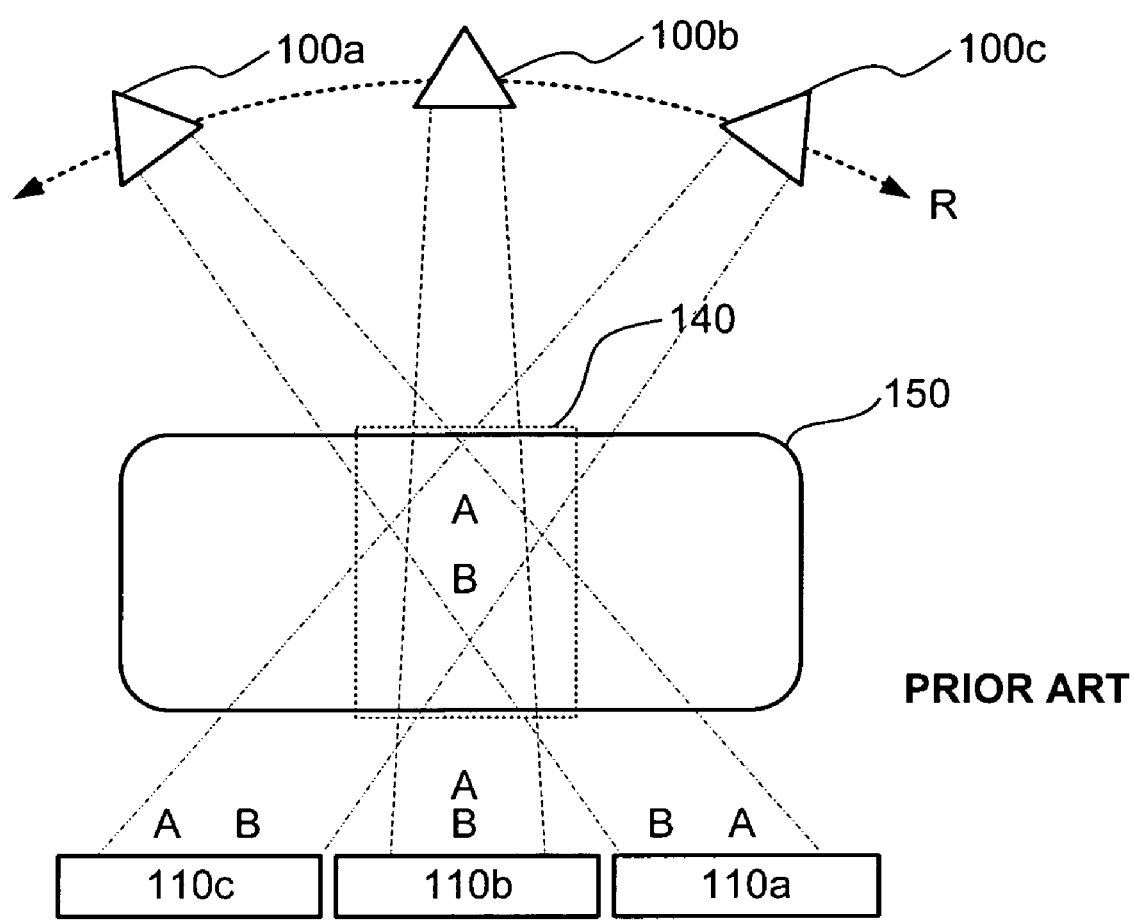
FIG. 1A (PRIOR ART) illustrates a conventional tomosynthesis imaging configuration.

FIG. 1A illustrates a conventional tomosynthesis imaging configuration. In such a conventional configuration, object 150 has a region of interest ("ROI") 140 where two features, A and B, are located at different depths within object 150. Object 150 is placed between an X-ray source located at any of positions 100a-c, and a detector located at any of positions 110a-c. Multiple images are then taken at the three different X-ray source and detector positions. For example, an image is taken with X-ray source position 100a and detector position 110a, X-ray source position 110b and detector position 110b, and X-ray source position 110c and detector position 110c. As a result, features A and B are recorded in a different location on the detector at each of detector positions 100a-c. It can be seen that if a 2-D X-ray image is desired, only one image need be taken at one of the desired positions.

As can be seen in FIG. 1A, the X-ray source is moved through positions 100a-c in a radial path, as depicted by arrow R. In some conventional configurations, such as in connection with CAT scans, the detector may be moved through positions 110a-c in a radial path as well. As was noted above, moving such components in a radial path often requires cumbersome, expensive and fault-prone equipment. For example, the apparatus of FIG. 1A not only requires a large field digital detector but also very accurate rotational motion control for a heavy X-ray tube in order to maintain high spatial resolution. If a user wishes to scan a different object, the apparatus must typically be reset to the original position. Such a requirement therefore renders the apparatus of FIG. 1A unsuitable for applications where continuous scanning is needed (e.g., airport security scanners).

Figure 1B:
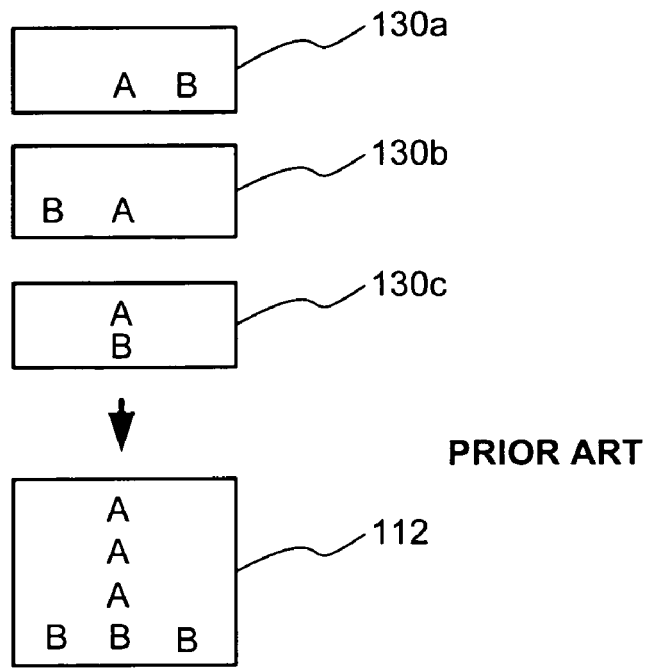
FIGS. 1B-C (PRIOR ART) illustrate an example shift and add imaging technique.
Figure 1C:
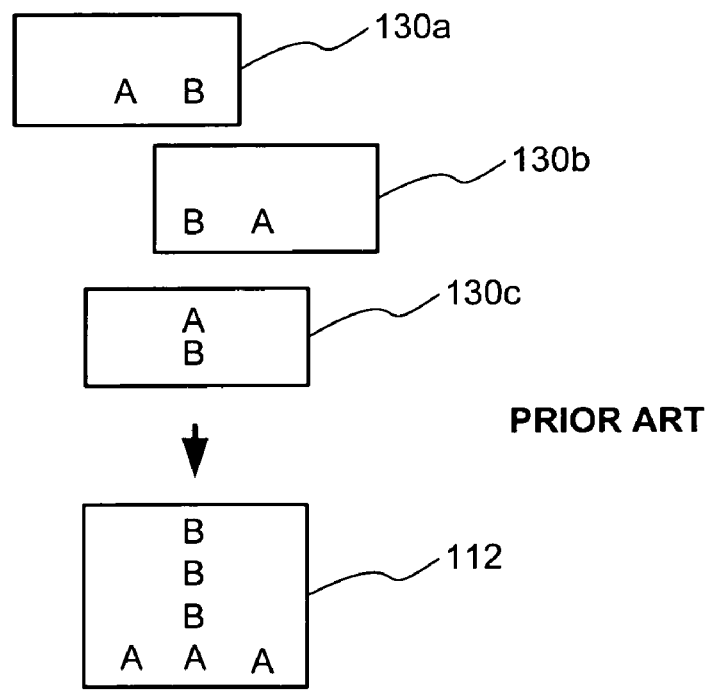

For further purposes of explanation and discussion, and referring now to FIGS. 1B-C, a conventional "shift and add" tomosynthesis imaging technique is illustrated. Such a technique is used to focus on different depths of an object to produce X-ray images of features located at such depths. For example, in FIG. 1B an image of feature A is to be produced. Thus, images 130a-c (corresponding to detector locations 100a-c, respectively) are aligned and "added" to produce output image 112. In output image 112, it can be seen that because feature A is in the same position in each image 130a-c, feature A has three superimposed images. In contrast, feature B is in a different location in each image 130a-c so the output image has only un-superimposed images of feature B.

As a result, feature A is emphasized while feature B is minimized, thereby producing an output image 112 that is focused at a depth within object 150 (not shown in FIG. 1B for clarity) that includes feature A.

Referring now to FIG. 1C, it can be seen that images 130a-c have been "shifted" to align feature B in each image. Thus, when adding the images 130a-c to produce output image 112, feature B will now be emphasized while feature A is minimized. Accordingly, output image 112 is focused at a depth within object 150 (not shown in FIG. 1C for clarity) that includes feature B. It will be appreciated that such shifting and adding is typically performed by computer, and that the representation of images 130a-c and output image 112 in FIGS. 1B-C is illustrated for purposes of explanation. It should also be noted that very complex algorithms may be used to reconstruct images at various depths having improved image quality.

Figure 2:
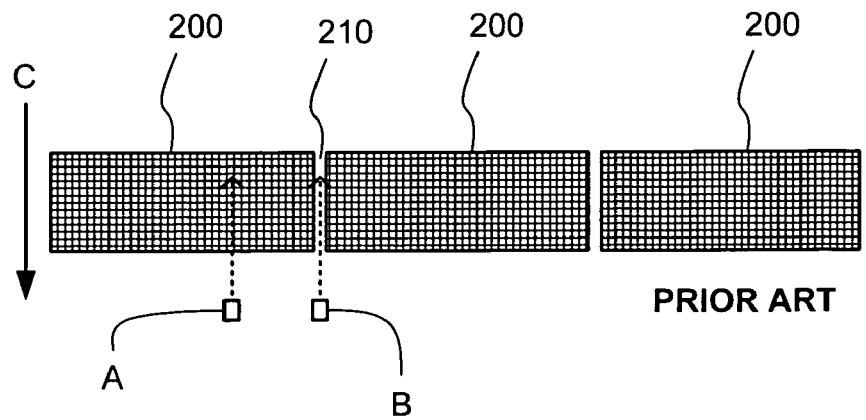
FIG. 2 (PRIOR ART) illustrates a conventional arrangement of small-field digital X-ray detectors.

FIG. 2 illustrates a conventional arrangement of small-field digital X-ray detectors 200. In such an arrangement, it can be seen that gap 210 is formed between each detector 200. Gap 210 can be minimized but not completely avoided between two adjoining detectors 200. For example, practical limitations prevent the electronics involved with detecting X-ray radiation from being extended completely to an edge of detector 200. In other words, the X-ray radiation-detecting portion of detector 200 is typically slightly recessed from an edge of the detector 200. In addition, internal electronics that generate electrical signals in response to the received X-ray radiation need to be connected to a processing device so an X-ray image may be generated. Thus, gap 210 may also include electrical interconnects.

Upon the relative movement between the detectors 200 and features A and B, feature A will be covered by a detector while feature B will pass through gap 210. Thus, an image of feature A may be generated, but feature B may pass undetected through detectors 200 because it happens to be positioned proximate gap 210. As can be seen, any information relating to features that pass through any of the gaps 210 between detectors 200 will be lost.

Figure 3A:
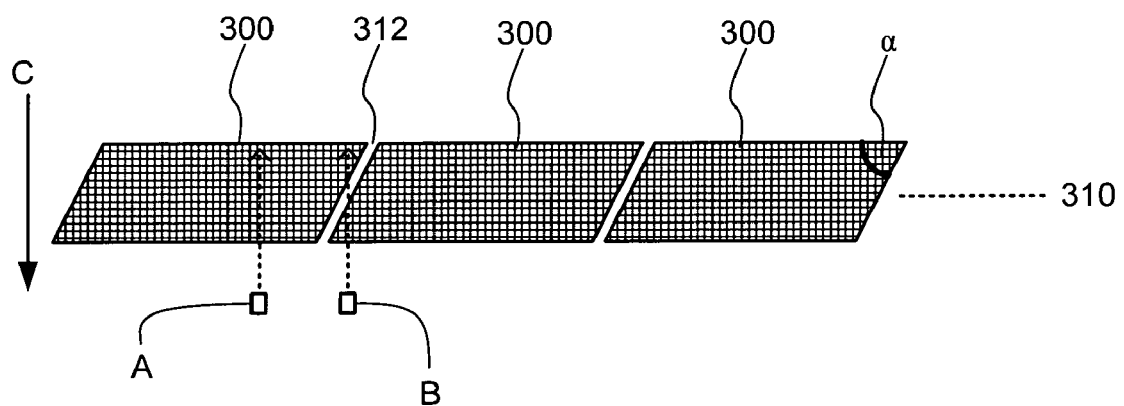
FIGS. 3A-G schematically show example arrangements of small-field X-ray detectors illustrating embodiments of the present invention.

Referring to FIG. 3A, an embodiment provides an array of adapted X-ray detectors that minimizes the information loss at each gap between detectors. Detectors 300 are configured such that a portion of each detector 300 extends outwardly, in parallel to a longitudinal axis formed by detectors 300 of array 310, so adjoining detectors 300 in array 310 overlap when viewed in direction C. In other words, a line drawn parallel to direction C that passes through gap 312 will intersect two adjoining detectors 300. As shown in FIG. 3A, detector module 300 consists of a 2-D matrix of smaller detection elements, or pixels. The layout of the 2-D pixels can be a normal horizontal/vertical matrix, or a matrix with its lines parallel to the corresponding sides of the example parallelogram. It can be seen that direction C is substantially perpendicular to the longitudinal axis formed by the detectors 300 of array 310, although direction C need not be perpendicular as will be discussed below in connection with FIG. 3I. While detectors 300 are illustrated in FIG. 3A as parallelograms, it will be appreciated that any configuration and/or shape of detectors 300 that permits some overlapping of detectors 300 when viewed in a desired direction of travel—whether actual travel or relative travel with respect to a moving object—are encompassed by the present invention. Non-limiting examples of different configurations and shapes are illustrated below in FIGS. 3B-F. If parallelogram-shaped detectors 300 are used in connection with an embodiment, it can be seen that any angle α that provides the above-noted overlapping may be used.

Detector array 310 preferably has a relatively narrow width and long length. When such a detector array 310 is moved in direction C relative to an object, the information loss due to gap 312 at a given image frame corresponding to a particular detector pixel or pixels can be compensated with the reading of other detector pixels from adjacent detectors 300 when those detector pixels scan across gap 312. In FIG. 3A, for example, feature B would be captured by both of the illustrated, adjoining detectors 300. The tiling direction and scanning geometry allow detector array 310 to obtain a complete data sampling for an entire region of interest ("ROI") of the object without loss of information. The individual small-field digital detectors may be any type of detector suitable for digital X-ray imaging such as, for example, CMOS (Complementary Metal-Oxide Semiconductor), a-Si (amorphous Si), CCD (charge-coupled device), photon-counting detectors such as CZT (CdZnTe), and the like. The term "relative motion" between objects as used herein refers to motion of either object while the other remains stationary and motion of both objects.

Figure 3B:
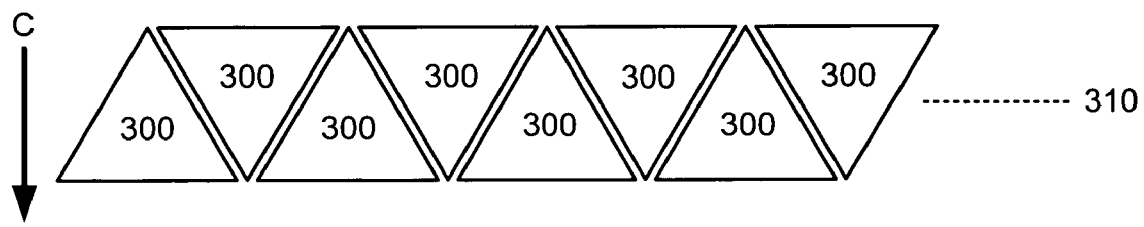
Figure 3C:
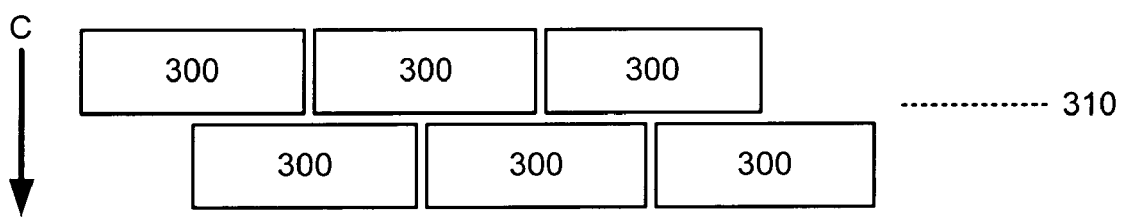
Figure 3D:
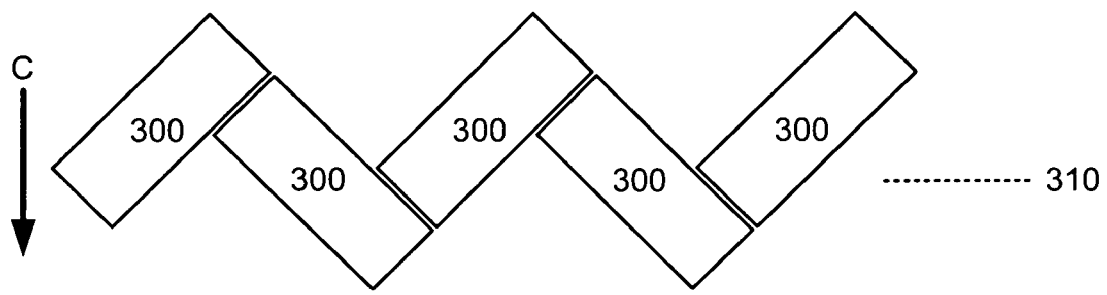
Figure 3E:
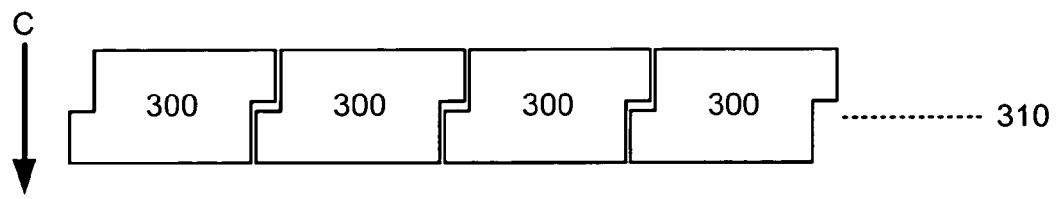
Figure 3F:
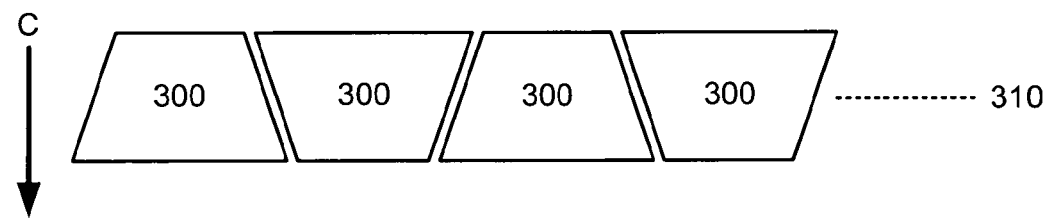

FIGS. 3B-F illustrate several different, non-limiting configurations of detectors 300 and arrays 310. For example, FIG. 3B illustrates triangular detectors 300 arranged in array 310. FIG. 3C illustrates two rows of rectangular detectors 300 arranged such that the combination of detectors 300 in both rows forms a single array 310. FIG. 3D illustrates angled, rectangular detectors 300 arranged to form array 310. FIG. 3E illustrates detectors 300 in the form of a polygon having a protrusion formed along a longitudinal axis formed by detectors 300 of array 310. FIG. 3F illustrates array 310 formed by a series of trapezoid-shaped detectors 300. In each of the configurations illustrated in FIGS. 3C-F, some combination of adjoining detectors 300 in array 310 overlap when viewed in direction C.

Figure 3G:
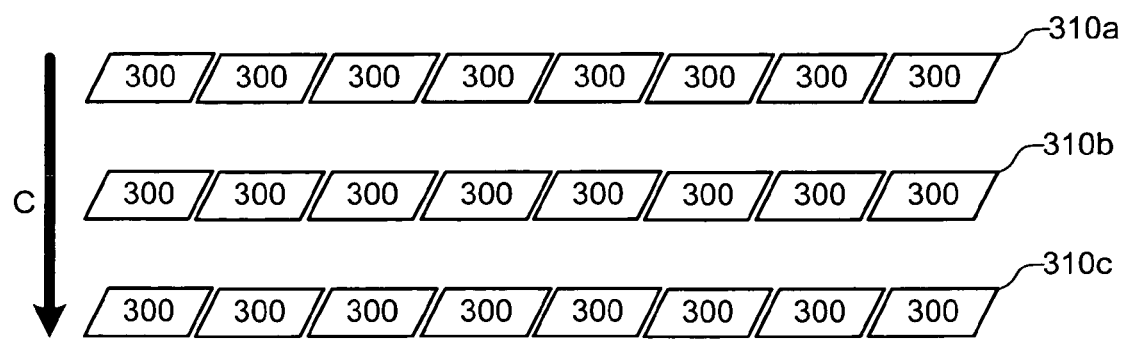

The present invention is not limited to a single array 310. For example, and referring now to FIG. 3G, arrays 310a-c are comprised of a plurality of detectors 300. When moved in direction C with a stationary X-ray source, each array 300a-c may pass over a ROI of an object, thereby enabling repeated data sampling at a predetermined projection angle from different detector arrays 310a-c. Direct summation of measured data for the same source-pixel angle enables noise reduction, and therefore achieves a higher X-ray utilization factor than is typically provided by, for example, a single slot scanning device, where only one array is present, or some other design in which only one linear array is present, (i.e., a 1-D pixel array that is perpendicular to the scanning direction). Any number of arrays 310 may be present. For example, 11 arrays may be used, while in another embodiment a smaller or greater number of arrays 310 may be used. The distance between each array 310a-c may be based on any number of factors such as, for example, space required for electrical interconnects, imaging requirements, and the like. The number and spacing of detector arrays 310 may be application-specific. For example, in a mammogram, an array length of 25-30 cm may be used at a spacing of 2 to 4 cm between two adjacent array centers, with a total of 10-15 arrays. The size of detector module 300 may be driven by a desire to minimize production costs.

Figure 3H:
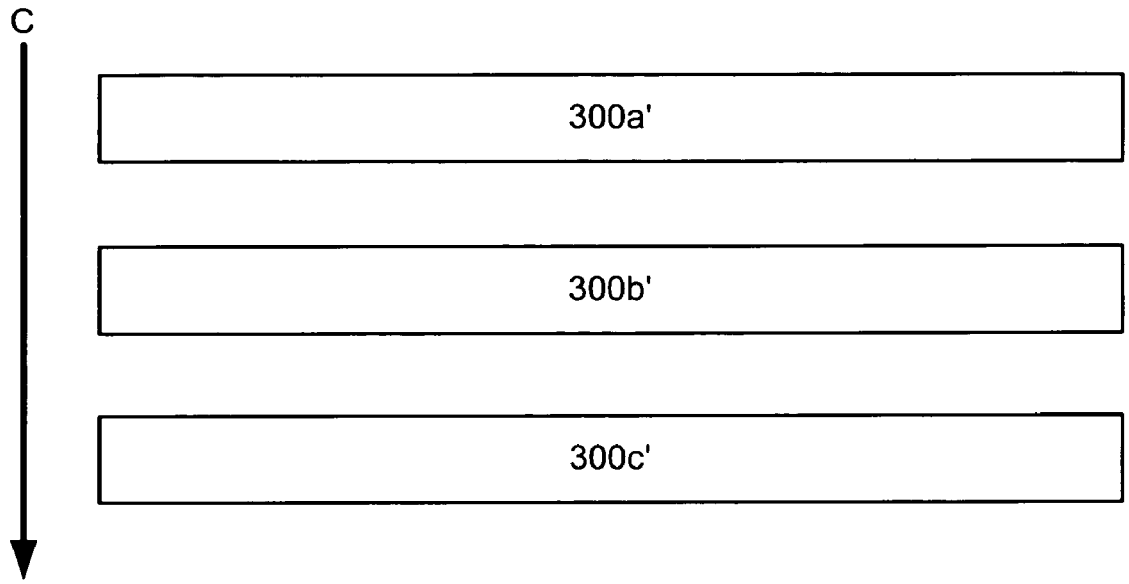
FIG. 3H illustrates an alternate example of X-ray detectors in accordance with an embodiment of the present invention.

Although FIGS. 3A-G and the corresponding discussion of digital X-ray imaging techniques pertain to detector arrays that are formed by more than one small-field digital X-ray detector, the present invention is not limited to the use of arrays formed by several small-field detectors. For example, FIG. 3H illustrates that a single, elongate, strip-like X-ray detector 300a' may be used in place of a detector array 310 having multiple detectors 300. The use of detector 300a', which preferably is positioned parallel to like elongate detectors schematically illustrated by detectors 300b' and 300c', eliminates the above-discussed gap between adjacent small-field detectors. Preferably, detectors 300a'-300c' span the width of the region of interest. Any number of elongate detectors, such as detectors 300a'-300c, may be used. Another embodiment may employ a large-field digital X-ray detector, which may be conventional. Thus, the present invention encompasses various configurations and sizes of detectors and/or arrays of detectors, and a digital X-ray image processing mechanism employed by a particular embodiment would account for the geometry that results from a choice of detector.

Figure 3I:
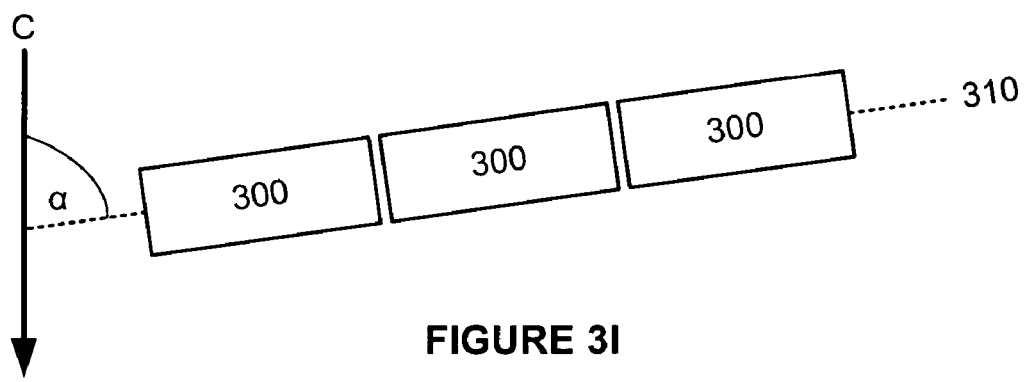
FIG. 3I schematically shows an example arrangement of small-field X-ray detectors illustrating an alternate embodiment of the present invention.

In FIGS. 3A through 3I, the direction of relative movement and scanning is the same as the direction C, which is the direction that portions of adjacent detectors overlap. FIG. 3I illustrates that a longitudinal axis formed by the detectors 300 of array 310 need not be substantially perpendicular to the direction of scanning. Rather, angle α formed between direction C (and also between the direction of relative movement and scanning) and the longitudinal axis of the array need not be 90° and may be any angle, provided that a digital X-ray image processing mechanism employed by a particular embodiment would account for the geometry that results from a choice of angle α. Although not illustrated in FIG. 3I, an embodiment also contemplates a single detector (as discussed above in connection with FIG. 3H, for example) that is formed such that a longitudinal axis is at an angle α with respect to direction C.

Methods of using such detectors in connection with both 2-D digital X-ray imaging and digital X-ray imaging involving tomosynthesis will now be discussed. Material decomposition techniques may be used in connection with any of such embodiments.

Figure 4A:
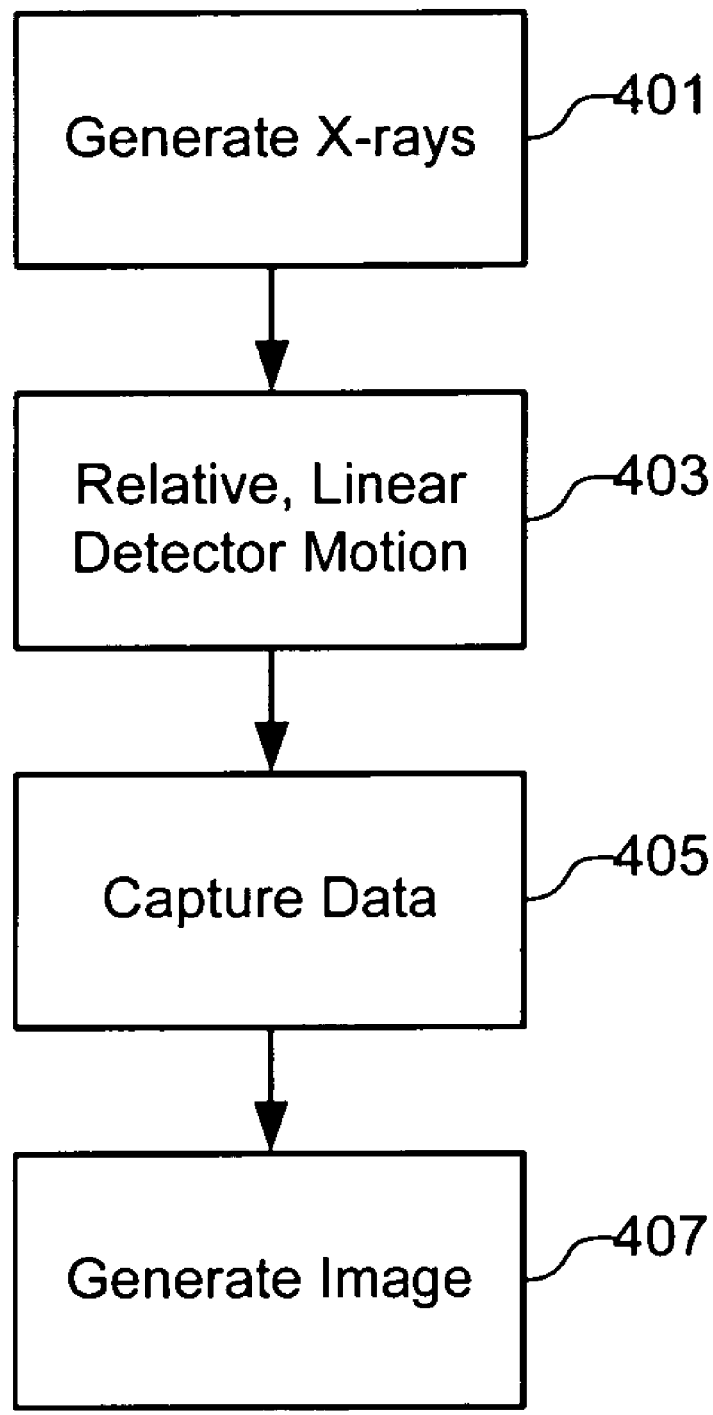
FIGS. 4A-B are flowcharts illustrating example X-ray imaging methods according to embodiments of the present invention.

Referring now to FIG. 4A, a flowchart illustrating an example method of using the above-described digital detector array in connection with 2-D X-ray imaging is provided. As was noted above, the figures and accompanying discussion that follows refer to using arrays of small-field detectors. The present invention, however, is not limited to the use of such detector arrays, as other types of detectors—including, for example, detector 300a'-c' of FIG. 3H, a single large-field detector, or several tiled or non-tiled conventional detectors—may be used.

At step 401, X-ray radiation is emitted by an X-ray source. The X-ray source may be any type of X-ray generating device that is suitable for the intended application. For example, an X-ray source used in connection with human and/or animal medical imaging may need to meet certain regulatory or guidelines concerning X-ray exposure and the like.

At step 403, an array of detectors, such as the detector arrays 310a-c discussed above in connection with FIG. 3G, are moved linearly across an object. It will be appreciated that, and as was noted above, such motion is relative to the object. Thus, the object may be moved, the array moved, or both. In addition, the relative linear motion may be substantially perpendicular to a longitudinal axis formed by the detectors in each array. An embodiment does not require perfect linear motion; however, substantially linear motion of the detector array simplifies the image processing algorithms used in connection with step 407, to be discussed below. In addition, the motion of the detector arrays is relative to the X-ray source as well. In other words, in an embodiment, the arrays 310 are moved relative to both the object and the X-ray source, and the object and the X-ray source may be stationary with respect to each other.

At step 405, data is captured by receiving the emitted X-ray radiation using the detectors in the array(s) while they are experiencing linear motion relative to the object. The data may be captured while the detectors are moving, or while the detectors are stopped at a desired position. The distance between two consecutive data acquisition positions may be determined by application-specific factors. In one such embodiment, the distance may be any value that is less than the width of a single detector array.

At step 407, an X-ray image is generated based on the known geometry of the detector arrays, distance from the X-ray source, and the like. Such image generation may involve any type of computer processing to convert the electrical data generated by the detectors in response to the received X-ray radiation that has passed through the object into a visual image.

Figure 4B:
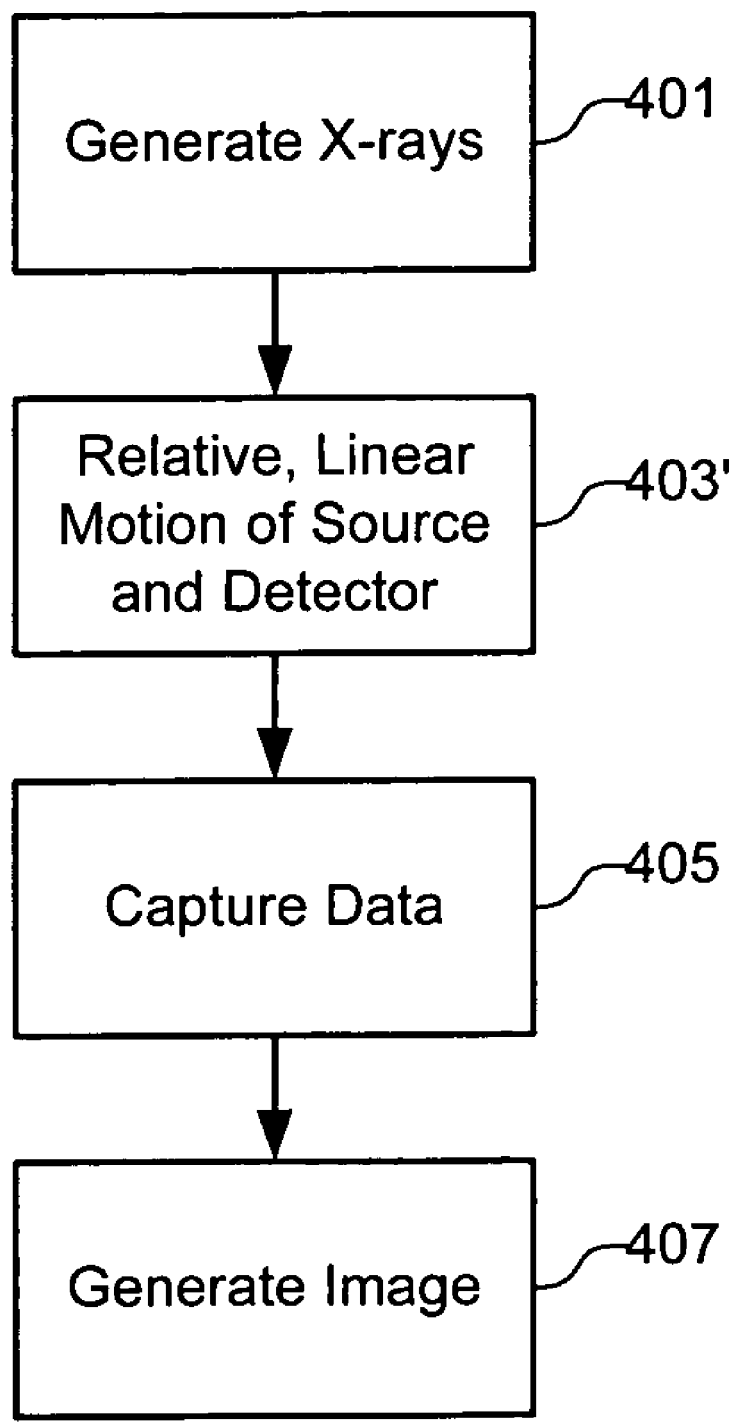

FIG. 4B illustrates an example method of producing digital X-ray imagery using tomosynthesis. At step 401, X-ray radiation is generated as was discussed above in connection with step 401 of FIG. 4A. At step 403', however, both the X-ray source and the detector arrays are moved linearly relative to the object, and may be stationary with respect to each other. At step 405, therefore, each detector array captures complete projection data at a different angle as the array and X-ray source move across the object. A detailed description of such geometry is provided below in connection with FIG. 7. At step 407, the captured data is processed to generate an image using any applicable data processing technique. For example, the shift and add technique described above may be used with modifications to accommodate the X-ray data that is acquired with linear relative motion.

Figure 5A:
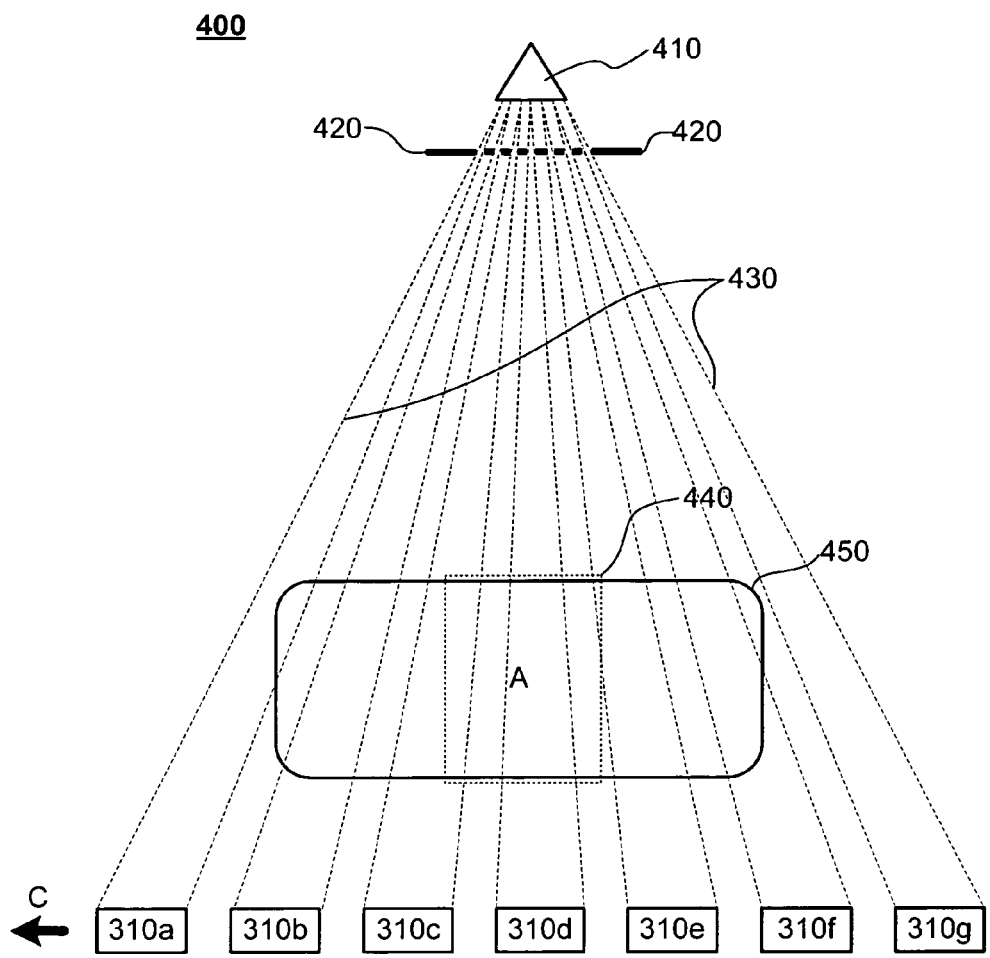
FIG. 5A illustrates an example X-ray imaging configuration according to an embodiment of the present invention.
Figure 5B:
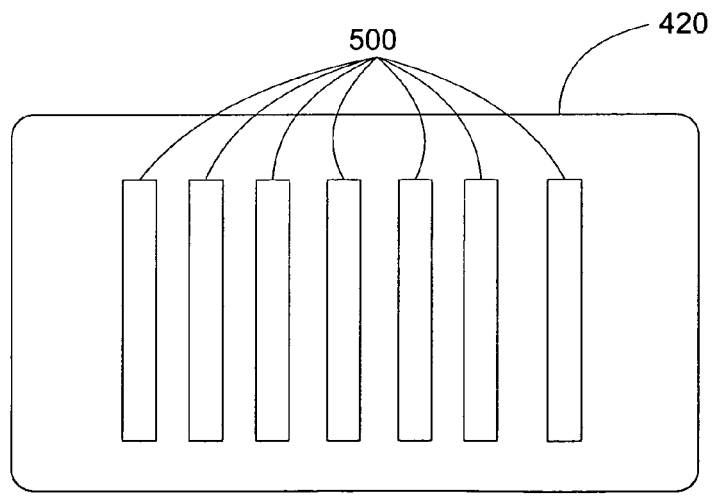
FIG. 5B illustrates an example collimator according to an embodiment of the present invention.

Now that example methods of generating digital X-ray imagery with the above-noted detector arrays have been discussed, example device configurations for carrying out such methods will now be described. Referring now to FIG. 5A, apparatus 400 has X-ray source 410, which is capable of generating X-ray radiation 430 for purposes of creating a 2-D digital X-ray image of ROI 440 containing feature A of object 450. Collimator 420 may be used to restrict X-ray radiation 430 to a desired region such as, for example, a region corresponding to the location of digital X-ray detector arrays 310a-g. An example collimator 420 is illustrated in FIG. 5B. Collimator 420 is shown as viewed from the position of X-rays source 410, and includes a plurality of filters 500. Collimator 420 may also be used for purposes of reducing extraneous X-ray radiation 430 exposure to object 450, which may be of particular importance if object 450 is a living organism. Referring again to FIG. 5A, the boundary lines of X-ray radiation 430 illustrate the reduced range of such X-ray radiation 430 caused by collimator 420. In addition, collimator 420 may be designed to have a pattern similar to that of detector arrays 310a-g, such that object 450 is only exposed to X-ray radiation 430 when arrays 310a-g are to be exposed to such X-ray radiation 430.

Complete blocking of X-rays that would not reach detector arrays 310a-g may be achieved by collimator 420, which may typically be fabricated from a heavy metal. Synchronous linear motion of collimator 420 with detector arrays 310a-g and X-ray source 410 may be needed for collimator 420 to direct X-rays only to detector arrays 310a-g that are active at any given time during data acquisition.

As can be seen in FIG. 5A, detector arrays 310a-g may be moved in direction C relative to object 450. Any mechanism for causing such relative linear motion may be used. Also, seven detector arrays 310a-g are shown in FIG. 5A for purposes of explanation, but it will be appreciated that any number of detector arrays 310 may be used. In addition, it will also be appreciated that the components of apparatus 400 may be mounted to an assembly that enables linear motion of detector arrays 310a-g, object 450 or both. For example, apparatus 400 may be mountable to an examination table so a patient may lie down and have the detector arrays 310a-g move linearly across his or her body. Alternatively, patient may be moved in unison with X-ray source 410, relative to detector arrays 310a-g. Regardless, any such configuration of apparatus 400, whether for medical or other applications, is equally consistent with an embodiment.

Figure 6A:
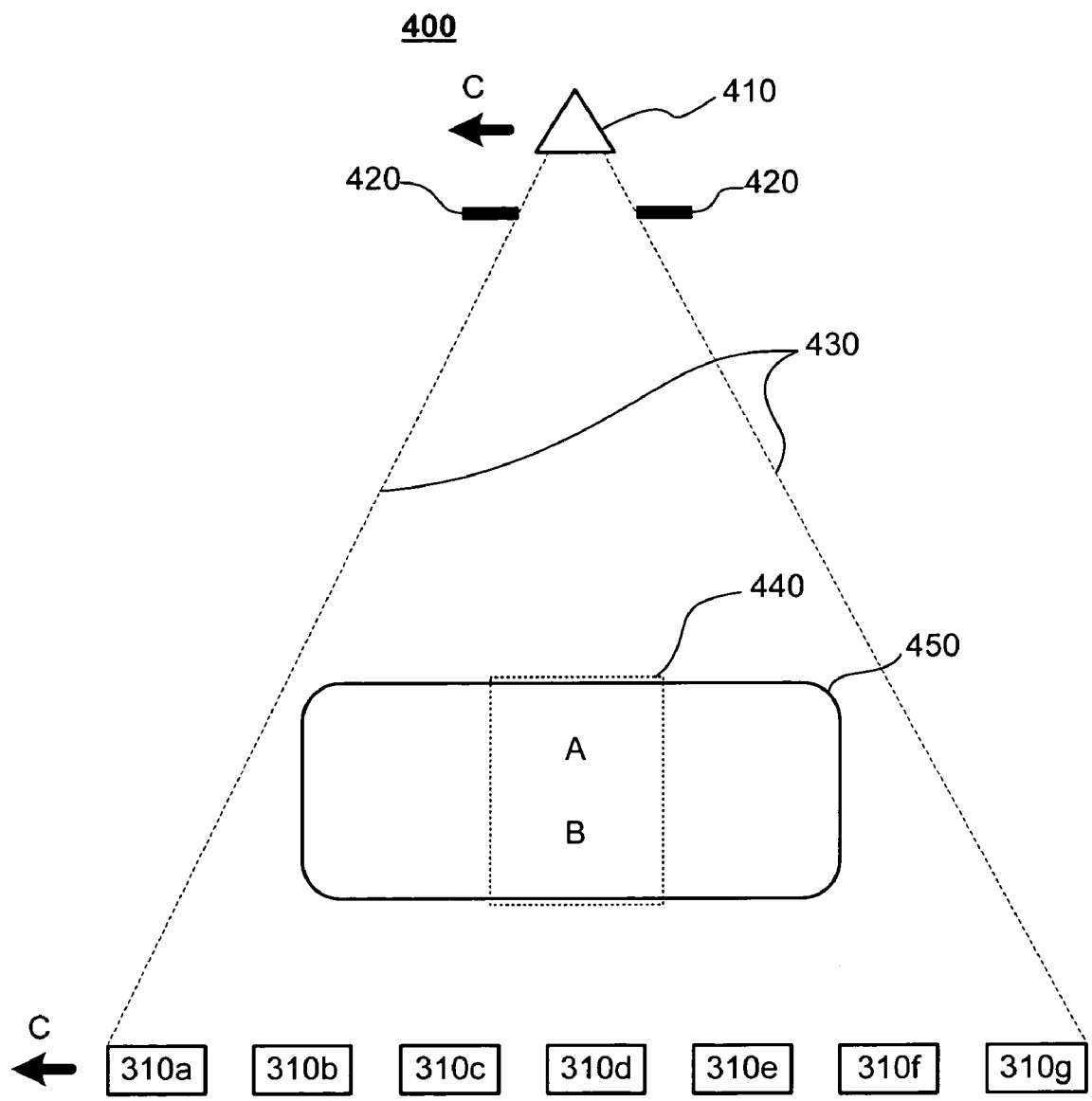
FIGS. 6A-B illustrate example X-ray tomosynthesis configurations according to an embodiment of the present invention.

Referring now to FIG. 6A, it can be seen that apparatus 400, including X-ray source 410, collimator 420 (details of collimator 420 are not shown in FIG. 6A for clarity), X-ray radiation 430, ROI 440 of object 450 and detector arrays 310a-g, are as was described above in connection with FIG. 5A. In addition, ROI 440 contains features A and B, which are each located at different depths within object 450. Thus, in the embodiment illustrated in FIG. 6A, an example configuration for purposes of carrying out a tomosynthesis imaging method is provided. X-ray source 410 also moves in unison with detector arrays 310a-g and collimator 420, for example in the manner discussed above in connection with FIG. 4B. As was noted above in connection with FIG. 5A, the components of apparatus 400 may be mounted to an assembly that enables linear motion of detector arrays 310a-g, X-ray source 410, object 450 or both. In addition to the medical example discussed above in connection with FIG. 5A, apparatus 400 may be used in connection with security, where material (e.g., luggage, packages, shipments, etc.) may be passed between X-ray source 410 and detector arrays 310a-g on a conveyor belt or the like. Apparatus 400 may be employed for medical, security or other applications without limitation.

Figure 6B:
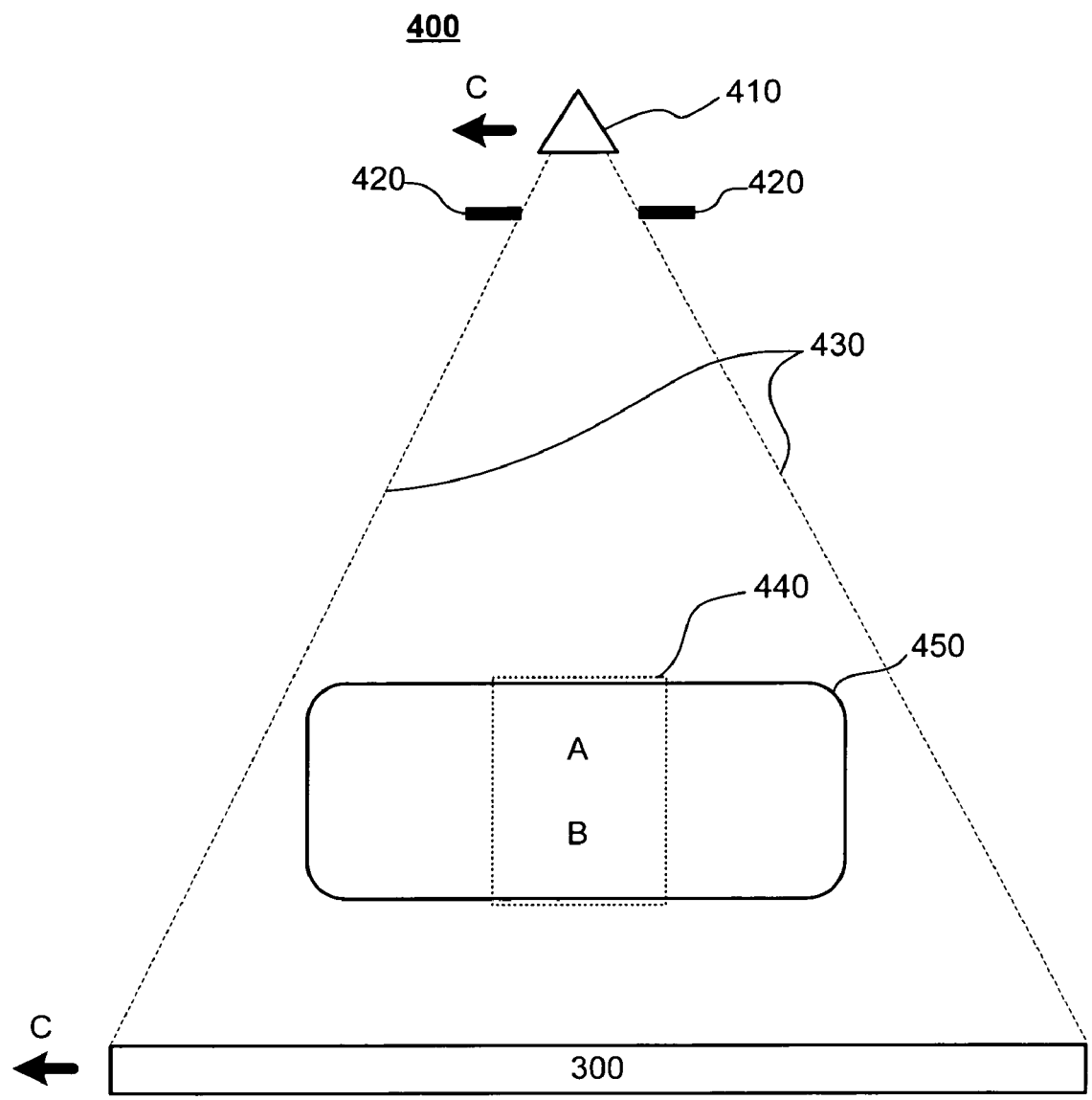

As noted above in connection with FIG. 3H, the present system and method may use a single, elongate, strip-like X-ray detector in place of a detector array 310a-g having multiple detectors 300. In addition, an alternative embodiment may employ a single large-field digital X-ray detector. To further illustrate that the present invention encompasses various configurations and sizes of detectors and/or arrays of detectors, FIG. 6B illustrates apparatus 400 as using a single detector 300 in place of the detector arrays 310a-g that were illustrated in FIG. 6A. While apparatus 400 may be used in connection with tomosynthesis, embodiments contemplate the use of a large-field detector 300 in connection with, for example, 2-D X-ray imaging.

Figure 7:
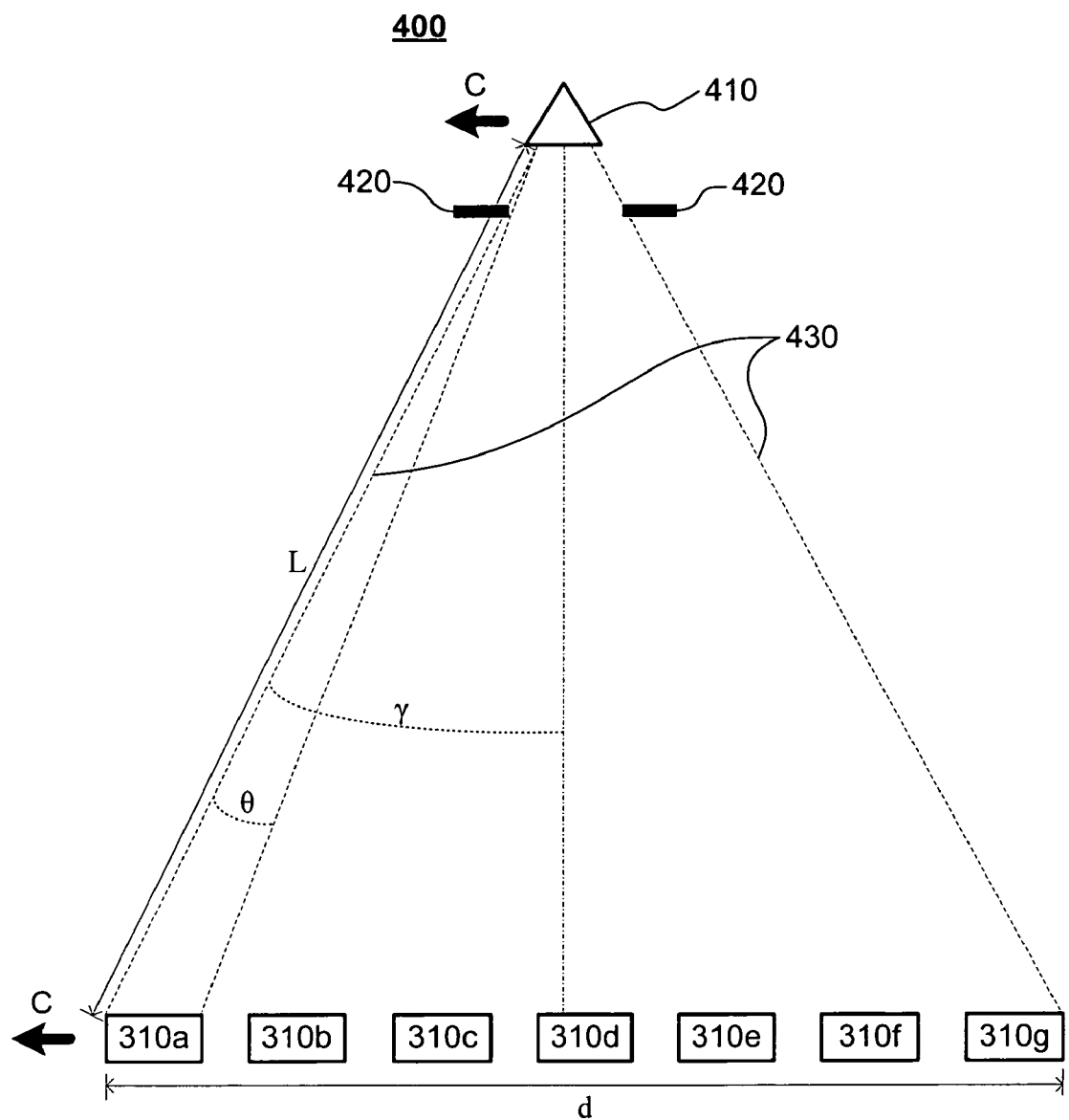
FIG. 7 illustrates an alternate example X-ray tomosynthesis configuration according to an embodiment of the present invention.

For purposes of better illustrating example geometric aspects, FIG. 7 is a detail view of the example configuration of FIG. 6A, which shows a series of detector arrays 310a-g. Apparatus 400, including X-ray source 410, collimator 420, X-ray radiation 430 and detector arrays 310a-g, are as described above in connection with FIG. 6A. ROI 440 of object 450 has been removed. The description below also applies to a configuration employing strip-like detectors 300a' et seq., which are schematically shown in FIG. 3H. And a person familiar with digital X-ray technology after reading the present disclosure will understand the application of the description below to configurations employing only a single, large-field detector or employing several tiled or non-tiled large-field detectors.

As can be seen in FIG. 7, divergence angle θ represents the divergence angle of X-ray radiation 430 that is incident on detector array 310a, distance L represents the distance between detector array 310a and X-ray source 410, distance d represents the distance between the first detector array 310a and the last detector array 310g and projection angle γ represents the deviation of X-ray radiation 430 from a centerline drawn from X-ray source 410 perpendicular to the plane of detector arrays 310a-g. Values for such angles and distances may be chosen in connection with image processing algorithms that may be employed to generate digital X-ray images from data collected by apparatus 400. While FIG. 7 illustrates seven detector arrays 310a-g, any number of detector arrays 310 may be present. For example, in some embodiments 10 to 15 detector arrays, or more, may be present. The space between the detector arrays 310a-g may be left for electronic readout interconnections or the like. X-ray source 410 and detector arrays 310a-g may be configured to scan in unison across a ROI of an object (e.g., a patient or the like). For example, such synchronized scanning may be provided by mounting X-ray source 410 and detector arrays 310a-g on the same assembly (not shown in FIG. 7 for clarity).

As X-ray source 410 and detector arrays 310a-g move linearly to scan across the ROI, each detector array 310a-g may provide a number of complete projection images with the narrow divergence angle θ at a projection angle γ with respect to the centerline. Projection angle γ is different for each detector array 310a-g. For example, assuming an X-ray source 410 to detector array 310a distance L of 500 mm, and a distance d from array 310a to array 310g of 300 mm, an approximately 32-degree angular divergence between array 310a and 310g may be achieved. Using, for example, a shift and add reconstruction method as was described above, one can observe features at different depths within an object, such as features A and B illustrated in FIG. 6, above. In some embodiments, 2-D digital X-ray imaging and tomosynthesis may be performed using the same apparatus 400, while in other embodiments such imaging may take place on specialized machines that perform one task or the other.

Furthermore, and as was noted above, material decomposition may also be achieved in connection with any of the embodiments described herein, whether such an embodiment is being used to acquire 2-D X-ray imagery or X-ray imagery involving tomosynthesis. In general, to obtain the material specificity required to perform material decomposition, two images with distinct incident energy spectra need to be acquired. Corresponding pixels in the two images should represent the exact X-ray path. For example, the two images corresponding to two incident X-ray spectra may be obtained with a photon-counting detector system where each individual photon event is recorded together with its energy information. For example, CZT is capable of performing such a task.

Alternatively, and as will be described herein, filters may be employed. Two types of beam filters may be used: one for aggressively attenuating the X-ray radiation at low energy, for example a copper (Cu) filter, and another for moderately attenuating low energy photons while aggressively attenuating high energy photons, for example a k-edge filter such as tungsten (W). By arranging such filters alternatively on the detector arrays, neighboring detector arrays will see different incident X-ray spectrum. By using a proper material decomposition processing algorithm, bone and soft tissue (for example) can be separated into two different images, as should be known to one of skill in the art.

Figure 8A:
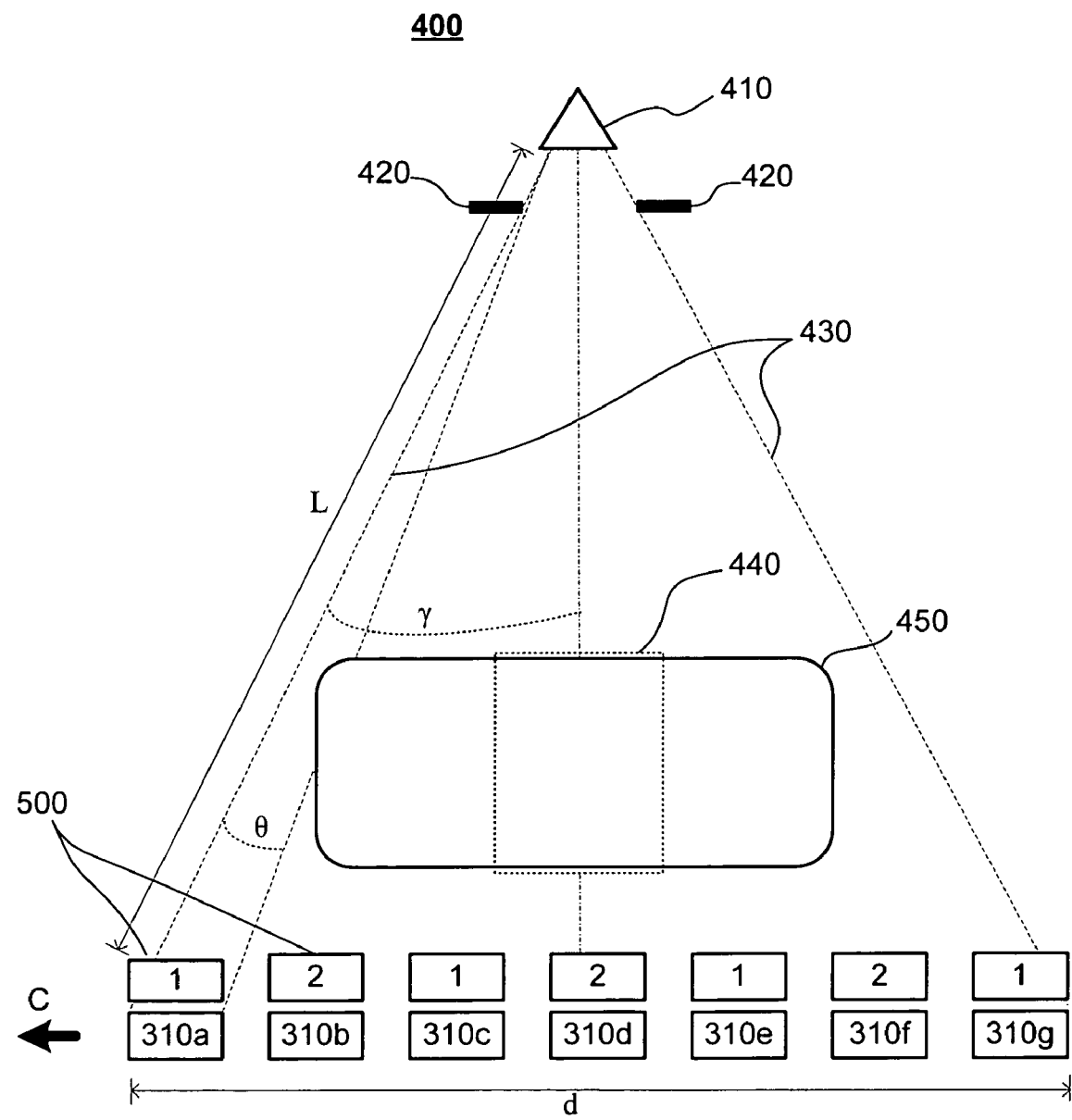
FIG. 8A illustrates an example material decomposition configuration for radiography according to an embodiment of the present invention.
Figure 8B:
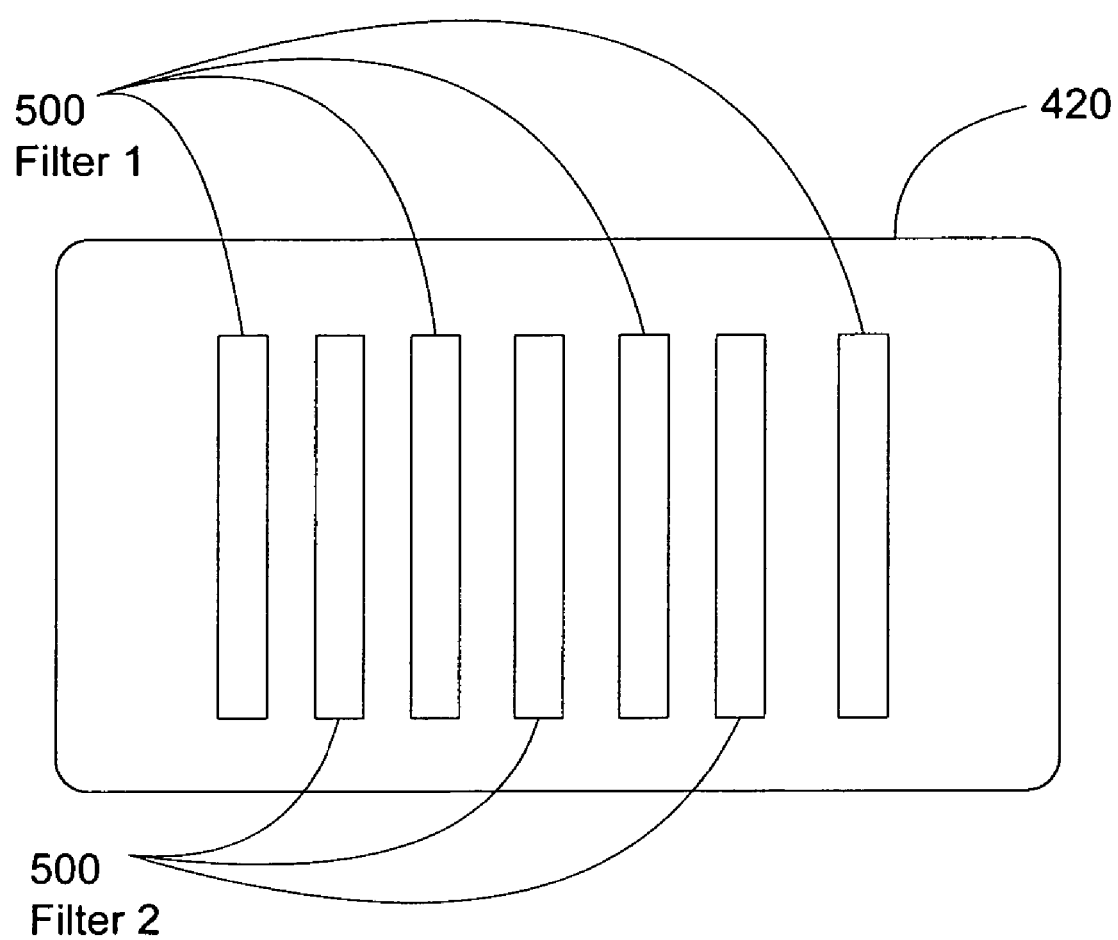
FIG. 8B illustrates an example filter according to an embodiment of the present invention.

Thus, and turning now to FIG. 8A, an example configuration enabling material decomposition is illustrated. It will be appreciated that the example configuration of FIG. 8A is generic for purposes of explanation. As can be seen in FIG. 8A, apparatus 400, including X-ray source 410, collimator 420, X-ray radiation 430, ROI 440 of object 450 and detector arrays 310a-g, are as was described above in connection with FIG. 5A. In addition, filters 500 are placed proximate each detector array 310a-g, or proximate X-ray source 410. FIG. 8B illustrates the latter configuration, with filters 500 incorporated into the design of collimator 420. In an embodiment, filters 500 may be used to reduce X-ray exposure to subject 450.

Returning now to FIG. 8A, filters 500 are comprised of filter material 1 and 2 that alternates for each array 310a-g.

The dimensions of each filter 500, and the composition of each filter material 1 and 2, may depend on the desired application. For example, in some embodiments filter materials 1 and 2 may be comprised of Copper and Tungsten, respectively, while other materials may be used in connection with other embodiments.

The purpose of the different beam filters is to create two distinct incident X-ray beam spectra, such that material decomposition can be applied to scanned object 450, which can enable improved image quality, particularly in connection with the difficult-to-image field of mammography and the like. In FIG. 8A, as detector arrays 310a-g scan across object 450, each detector array 310a-g produces an image at the same projection angle and location for object 450. Thus, images produced by detector array 310a-g are all the same, except that the images produced by adjacent detector arrays are with two different filters (e.g., materials 1 and 2). These two images can be processed to generate, for example, material-specific images through basis material decomposition. Furthermore, images obtained with arrays seeing the same filter material can be averaged to reduce image noise. In addition, the two reduced-noise images with two different filters may be further processed for basis material decomposition, or effective atomic number Z calculation.

In an embodiment where material decomposition of a 2-D X-ray image is desired, there is a relative position change between X-ray source 410, filter 500 and detector arrays 310a-g. In addition, collimator 420 and filter 500 may follow the motion of detector arrays 310a-g. Thus, collimator 420, filter 500 and detector arrays 310a-g may move in unison such that X-ray radiation 430 beams emanating from collimator 420 follow the movement of detector arrays 310a-g. It will be appreciated that a beam blocking device may be a part of or in addition to collimator 420 to block X-ray radiation 430 that exits collimator 420 and would otherwise irradiate outside the object's 450 ROI 440.

Figure 9A:
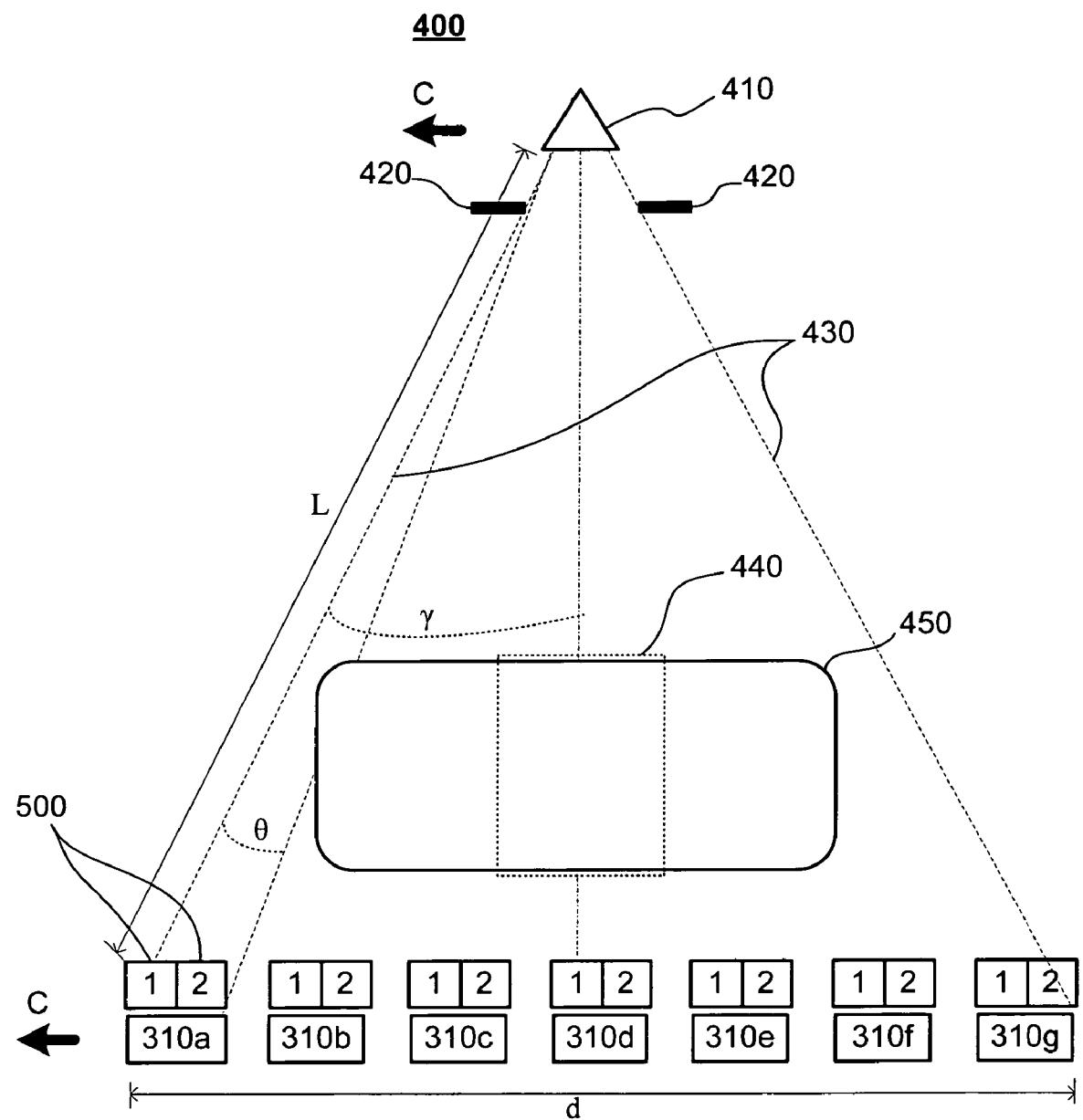
FIG. 9A illustrates an alternate example material decomposition configuration for radiography according to an embodiment of the present invention.
Figure 9B:
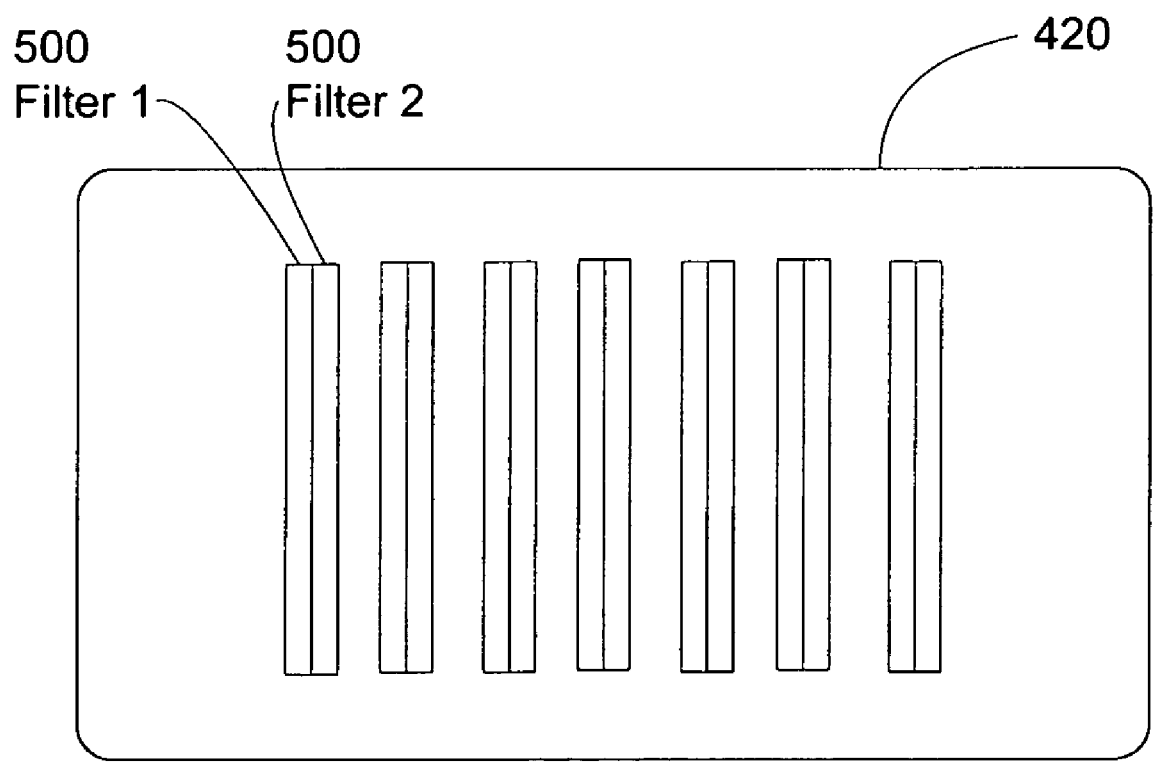
FIG. 9B illustrates an alternate example filter according to an embodiment of the present invention.

FIG. 9A illustrates just one alternate configuration of apparatus 400 where filter 500 is near detector arrays 310a-g, as shown, or located proximate X-ray source 410. FIG. 9B illustrates the latter configuration, with filters 500 incorporated into the design of collimator 420.

Returning now to FIG. 9A, X-ray source 410, collimator 420, X-ray radiation 430, ROI 440 of object 450 and detector arrays 310a-g are as was described above in connection with FIGS. 5A and 8A. Unlike filter 500 depicted in FIGS. 8A-B, however, each filter 500 is comprised of both filter materials 1 and 2. In this configuration, filter 1 covers half of any array 310a-g and filter 2 covers the other half of the same array 310a-g, as depicted in FIG. 9. This arrangement minimizes the relative angle between the X-ray projections from two different filters 500 and X-ray source 410, which is θ/2. Thus, this configuration is more appropriate for a tomosynthesis scanning mode, in which the relative angle between detector array 310a-g and X-ray source 410 remains unchanged.

As stated earlier, to perform basis material decomposition, two projection images are acquired for the same projection path through ROI 440 of object 450. Typically, detector arrays 310a-g are narrow in width, so the small divergence angle θ/2 can be corrected or ignored when images acquired by the first and second halves of detector array 310a-g are used for basis material decomposition. After basis material decomposition, these two projection images can again be processed to form two tomosynthesis images at a given depth, where each image corresponds to a basis material. It will be appreciated that any number of materials and configurations of filter 500 are possible, and such configurations may be based on any number and type of considerations. For example, the configuration of apparatus 400 illustrated in FIG. 9A may be to enable easy removal and/or insertion of filter 500 so as to enable apparatus 400 to generate X-ray images with and without material decomposition.

The subject matter of embodiments of the present invention has been described with specificity to meet statutory requirements. However, the description itself, nor the information provided in the Background section, is not intended to limit the scope of this patent. Rather, the inventor has contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described. Also, it is to be understood that other, similar embodiments may be used or modifications and additions may be made to the described embodiment for performing the same function of the present invention without deviating therefrom. Further, the information in the Background and Detailed Description sections relating to conventional technology or drawbacks thereof is not intended to limit the scope of the invention nor to distinguish subject matter from the present invention. The present invention should not be limited to any single embodiment, or by the discussion of conventional technology, but rather should be construed in breadth and scope in accordance with the appended claims.

What is claimed:

1. An X-ray device for tomosynthesis, the device comprising:
    an X-ray source for emitting X-ray radiation at an object in a first direction; and
    at least one digital X-ray detector array having a plurality of detectors, each detector comprising a two-dimensional matrix of detection elements, wherein the at least one detector array is located on a substantially opposite side of the object from the X-ray source, wherein a line parallel to a scanning axis intersects at least two of the plurality of detectors in the detector array, and wherein the at least one detector array is configured such that it:
        moves, in a single pass, linearly relative to the object along the scanning axis which is substantially perpendicular to the first direction;
        receives, during the single pass, X-ray radiation that has passed through a region of interest of the object from a plurality of incident angles; and
        provides, based on the X-ray radiation received during the single pass, an electronic signal that represents an X-ray image of the region of interest.

2. The device of claim 1, wherein the detectors of each detector array are arranged along a longitudinal axis.

3. The device of claim 2, wherein the array longitudinal axis is substantially perpendicular to the scanning axis.

4. The device of claim 2, wherein the longitudinal axis is oblique to the scanning axis.

5. The device of claim 1, wherein each of the plurality of detectors contains pixels for receiving X-ray radiation.

6. The device of claim 1, wherein the plurality of detection elements are pixels for receiving X-ray radiation.

7. The device of claim 1, wherein a first detector is adjacent to a second detector that has a boundary edge that opposes a boundary edge of the first detector.

8. The device of claim 7, wherein the opposing boundary edges are parallel.

9. The device of claim 8, wherein each detector has a shape selected from the group consisting of: a parallelogram, a trapezoid, a rectangle, a triangle and a polygon having a protrusion formed along a longitudinal axis that is substantially perpendicular to the scanning axis.

10. The device of claim 1, wherein a first detector has a boundary edge that is oblique to the scanning axis.

11. The device of claim 1, further comprising a collimator for blocking emitted X-ray radiation.

12. The device of claim 1, further comprising a first filter and a second filter material for attenuating the emitted X-ray radiation.

13. The device of claim 12, wherein the first and second filter materials each provide a different attenuation of the emitted X-ray radiation.

14. The device of claim 12, wherein the first and second filter materials are disposed proximate the X-ray source.

15. The device of claim 12, wherein the first and second filter materials are disposed proximate the at least one detector array.

16. The device of claim 12, wherein the first filter material is substantially comprised of Copper and the second filter material is substantially comprised of Tungsten.

17. The device of claim 1, wherein the X-ray source and object are stationary while the at least one detector array moves relative to the object along the scanning axis.

18. The device of claim 1, wherein the generated electronic signal is used to generate a 2-D X-ray image.

19. The device of claim 1, wherein both the X-ray source and the at least one detector array move in unison along the scanning axis relative to the object in the single pass.

20. The device of claim 19, wherein the X-ray image is generated from the electronic signal using tomosynthesis.

21. The device of claim 19, wherein the X-ray image is a 2-D X-ray image of a predetermined depth within the region of interest of the object.

22. An X-ray imaging method for tomosynthesis, the method comprising:
    emitting X-ray radiation toward an object in a first direction;
    causing relative linear motion between at least one digital X-ray detector array and the object, wherein the relative linear motion is along a scanning axis that is substantially perpendicular to the first direction and occurs in a single pass and wherein the at least one detector array has a plurality of detectors arranged such that a line parallel to the scanning axis intersects at least two of the plurality of detectors, each detector comprising a two-dimensional matrix of detection elements;
    receiving, during the single pass, X-ray radiation that has passed through a region of interest with the object and within a plurality of incident angles using the at least one digital X-ray detector array; and
    generating, based on the X-ray radiation received during the single pass, an electronic signal that represents an X-ray image of the region of interest.

23. The method of claim 22, further comprising causing relative linear motion between the X-ray source and the object.

24. The method of claim 23, wherein the relative linear motions of the at least one detector array and of the X-ray source occur in unison.

25. The method of claim 24, further comprising processing the electronic signal to generate a tomosynthesis image.

26. The method of claim 22, wherein a line parallel to the scanning axis intersects at least two detectors in said at least one detector array.

27. An X-ray device for tomosynthesis, the device comprising:
    a plurality of elongated digital detectors, each comprising a two-dimensional matrix of detection elements, the a plurality of elongated digital detectors including at least a first and a second elongated digital detector for receiving X-ray radiation received from a first direction, wherein the first and second elongated digital detectors are generally arranged adjacent to each other, and move, in a single pass, linearly along a scanning axis that is substantially perpendicular to the first direction, wherein the scanning axis represents a direction of movement of the detectors relative to an object to be analyzed, wherein the first and second elongated digital detectors are adapted to receive the X-ray radiation within a plurality of incident angles when moving along the scanning axis, and wherein the object to be analyzed is located between the plurality of elongated digital detectors and an X-ray source.

28. The x-ray device of claim 27, wherein the X-ray source moves relative to the object along the scanning axis in unison with the first and second elongated digital detectors.

29. The x-ray device of claim 27, wherein the first elongated digital detector is formed in a parallelogram shape.

30. The device of claim 12, wherein the single pass is a first single pass, and wherein the X-ray detector receives X-ray radiation that is attenuated by the first filter during the first single pass.

31. The device of claim 30, wherein the electronic signal is a first electronic signal, and the X-ray image is a first X-ray image, and wherein the X-ray detector further:
    moves, in a second single pass, linearly relative to the object along the scanning axis;
    receives, during the second single pass, X-ray radiation that has passed through the region of interest of the object and is attenuated by the second filter from the plurality of incident angles; and
    provides, based on the X-ray radiation received during the second single pass, a second electronic signal that represents a second X-ray image of the region of interest.

32. The device of claim 12, wherein the X-ray detector receives the X-ray radiation that is attenuated by the first filter and the second filter during the single pass.

33. The device of claim 1, wherein the single pass is a first single pass, and wherein the digital X-ray detector further performs said moving, receiving and providing in a second single pass.

34. An X-ray imaging method for tomosynthesis, the method comprising:
    emitting X-ray radiation toward an object in a first direction;
    causing relative linear motion between a plurality of elongated digital X-ray detectors and the object, wherein the relative linear motion is along a scanning axis that is substantially perpendicular to the first direction and occurs in a single pass and wherein each elongated X-ray detector comprises a two-dimensional matrix of detection elements;
    receiving, during the single pass, X-ray radiation that has passed through a region of interest with the object and within a plurality of incident angles using the plurality of elongated digital X-ray detectors; and
    generating, based on the X-ray radiation received during the single pass, an electronic signal that represents an X-ray image of the region of interest.

* * * * *